(12) United States Patent
Mitchell

(10) Patent No.: US 8,124,180 B2
(45) Date of Patent: Feb. 28, 2012

(54) THIN LAYER SUBSTRATE COATING AND METHOD OF FORMING SAME

(75) Inventor: John C. Mitchell, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 503 days.

(21) Appl. No.: 11/966,740

(22) Filed: Dec. 28, 2007

(65) Prior Publication Data

US 2008/0160193 A1     Jul. 3, 2008

Related U.S. Application Data

(60) Provisional application No. 60/883,302, filed on Jan. 3, 2007.

(51) Int. Cl.
| | |
|---|---|
| C23C 16/00 | (2006.01) |
| C23C 16/40 | (2006.01) |
| A61L 33/00 | (2006.01) |
| A61L 27/32 | (2006.01) |
| B05D 3/00 | (2006.01) |
| A61K 6/083 | (2006.01) |
| A61C 15/04 | (2006.01) |

(52) U.S. Cl. .......... 427/255.19; 427/2.1; 427/2.24; 427/2.26; 427/2.27; 427/2.29

(58) Field of Classification Search .......... 427/255.19, 427/2.1, 2.24, 2.26, 2.27, 2.29
See application file for complete search history.

(56) References Cited

U.S. PATENT DOCUMENTS

| | | | |
|---|---|---|---|
| 4,064,311 A | 12/1977 | McLean et al. | |
| 4,420,501 A * | 12/1983 | Ueda et al. | 427/514 |
| 5,785,876 A | 7/1998 | Fuesser et al. | |
| 2004/0121291 A1 | 6/2004 | Knapp et al. | |
| 2004/0224087 A1 | 11/2004 | Weimer et al. | |
| 2005/0110177 A1 * | 5/2005 | Schulman et al. | 264/16 |
| 2005/0221072 A1 | 10/2005 | Dubrow et al. | |
| 2006/0105297 A1 * | 5/2006 | Knapp et al. | 433/206 |
| 2006/0246149 A1 * | 11/2006 | Buchholz et al. | 424/603 |
| 2006/0251875 A1 * | 11/2006 | Carlisle et al. | 428/213 |
| 2007/0077349 A1 * | 4/2007 | Newman et al. | 427/66 |

FOREIGN PATENT DOCUMENTS

| | | |
|---|---|---|
| EP | 1 679 088 A2 | 7/2006 |
| EP | 1679088 A2 * | 7/2006 |
| WO | 2005/055870 A2 | 6/2005 |

* cited by examiner

*Primary Examiner* — Kelly M Gambetta
(74) *Attorney, Agent, or Firm* — Schwabe, Williamson & Wyatt

(57) ABSTRACT

Embodiments of the present invention relate to coating deposition and coatings for dental and orthopedic devices that provide prevention or reduction of ion leakage and, in some situations, improved aesthetic appearances.

21 Claims, 4 Drawing Sheets

THIN LAYER SUBSTRATE COATING AND METHOD OF FORMING SAME

CROSS REFERENCE TO RELATED APPLICATIONS

The present application claims priority to U.S. Provisional Patent Application No. 60/883,302, filed Jan. 3, 2007, entitled "Ion-Leakage Barrier Coating," the entire disclosure of which is hereby incorporated by reference in its entirety.

TECHNICAL FIELD

Embodiments of the present invention relate to the field of coatings and coating deposition, and, more specifically, to coatings for dental and orthopedic devices that provide prevention or reduction of ion leakage and, in some situations, improved aesthetic appearances.

BACKGROUND

Improved standards of living and better dental education over the past thirty years have given rise to higher expectations for dental treatment, for example, for safety, durability, and aesthetics. The higher standards demanded by adults are also being applied to their children. The demand for aesthetics and the requirement of durable and proven restorative care present a challenging balance that must be managed.

For over fifty years, stainless steel crowns (SSC) have proven to be some of the most durable and successful posterior restorations for primary teeth. They have been considered to be the best choice of treatment for teeth with multi-surface caries, developmental defects, fractured teeth, abutments for space maintainers and for the best conservation after root canal treatment in primary dentition.

Despite their durable clinical advantages, these types of restorations suffer from two major drawbacks: low aesthetic perception, and Ni-ion release.

Parents often express that they do not like the way that stainless steel crowns look, with the crowns on the lower first primary molars being commented on the most.

There have been several attempts at improving the aesthetics of stainless steel crowns. Open-faced SSCs were an attempt to use composite dental restorative material inserted into a cut window in the crown. The disadvantage of this method is that they are time consuming and the metal window and/or blood may cause discoloration of the composite, which ultimately reduces the aesthetic value.

Stainless steel crowns with bonded composite veneers have been developed as an alternative to open faced crowns. Composite may be bonded effectively to the metal of stainless steel crowns using a bonding agent. Fuks et al. (1999) reported that although aesthetics are improved, occlusal reduction has to be more aggressive, crimping is more difficult, the crowns have to fit passively to avoid facing fracture, the final aesthetic result is not always pleasing, and they are expensive.

If the crowns are being chosen for aesthetic value, the durability of the composite veneer is of clinical importance. Ram et al. (2003) reported that after 4 years, all aesthetic crowns presented chipping of the facing and, consequently, a very poor aesthetic appearance.

As a component of the stainless steel alloy from which they are fabricated, stainless steel crowns contain 9-12% Ni. Despite all the good properties resulting from the presence of nickel, it has a few contraindications for its use. Nickel allergic contact dermatitis is the most prevalent allergy in North America with an incidence of 14.3%. It is known to cause CFS like symptoms, chronic fatigue, fibromyalgia and other diseases of unknown etiology. Children between 8-12 years of age have been documented to have reported a positive patch test for nickel sensitivity (8.1%). 22.97% nickel in intraoral alloys seems to raise circulating eiosinophil, neutrophil and basophil numbers. Even though these crowns provide the best available conservation of the tooth, the Ni ion release from these alloys over time may cause lymphocytic reactivity leading to various major health issues in children.

Other dental and orthopedic devices and materials suffer from some of the same problems identified above with respect to stainless steel crowns.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

Figure 1A:
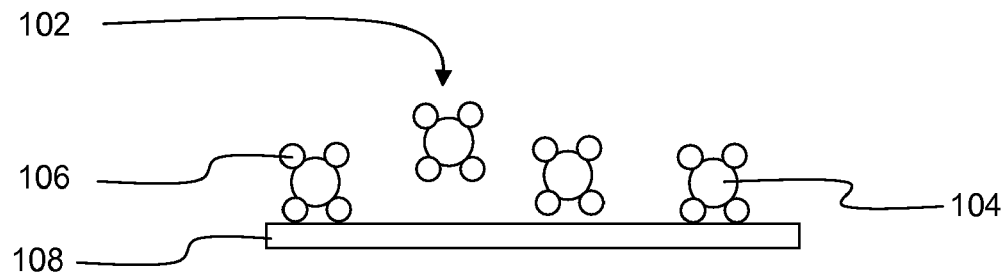
FIG. 1 illustrates a cycle of an exemplary atomic layer deposition method in a series of operations in accordance with various embodiments of the present invention.

In the following detailed description, reference is made to the accompanying drawings which form a part hereof, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods, apparatuses, and systems for providing thin film coatings for dental and/or orthopedic devices are provided.

In an embodiment, an atomic layer deposition (ALD) process may be utilized to provide coatings on dental alloys and orthopedic implants, and to provide ion-release prevention/reduction and/or increased aesthetic properties. As an example, reduction or prevention of release of ions may be beneficial in that certain ions, such as nickel, may cause allergic reaction.

An ALD coating may provide one or more very thin, conformal layers/films of a coating material. In an embodiment, an ALD coating may be optically transparent. In other embodiments, depending on the thickness of the coating, an ALD coating may exhibit interference colors. In an embodiment, an ALD coating may provide flexible, yet durable, coatings by selecting one or more suitable coating materials with which to coat, and by selecting a suitable number or thickness of the layer(s). In an embodiment, a suitable coating may be scratch resistant. In contrast, certain composite coatings used in traditional treatments may not be flexible and thus may crack or break under stress or strain. In addition, various known composite coatings and deposition methods form porous coatings with holes that allow for passage of ions through the coating. The passage of ions through the coating can cause problems as discussed above, resulting in, for example, nickel ion leakage. Embodiments of the present invention address this problem by providing coatings and deposition processes that reduce or eliminate ion leakage. In an embodiment, coatings may be provided that are free of pinholes or other channels through which ions may leak.

In an embodiment, ALD sequentially introduces various reactants in a gas phase to form successive monolayers of film from the surface up, allowing for thickness control and repeatability. In an embodiment, an ALD process provides pinhole free surface layers.

In an embodiment, a substrate or surface may be exposed to alternating and sequential pulses of at least two mutually reactive reactants. In an exemplary ALD process, two or more precursor gases flow over a surface in an alternating manner, so that the gases react with the sites or functional groups on the surface. When all of the available sites are saturated, the reaction stops and an inert gas flow purges the excess precursor molecules from the region. The process is repeated as the next precursor gas flows over the surface. A cycle is defined as one pulse of the first precursor, purge, one pulse of the second precursor, purge, and so on. This sequence may be repeated until the final desired thickness is reached. These sequential, self-limiting surface reactions result in one monolayer of deposited film per cycle.

Thus, in an embodiment, a method of coating a substrate for use in a dental or orthopedic device is provided comprising providing a substrate, and forming at least one thin film layer on a surface of the substrate by atomic vapor deposition to coat at least a portion of the surface of the substrate.

Figure 1B:
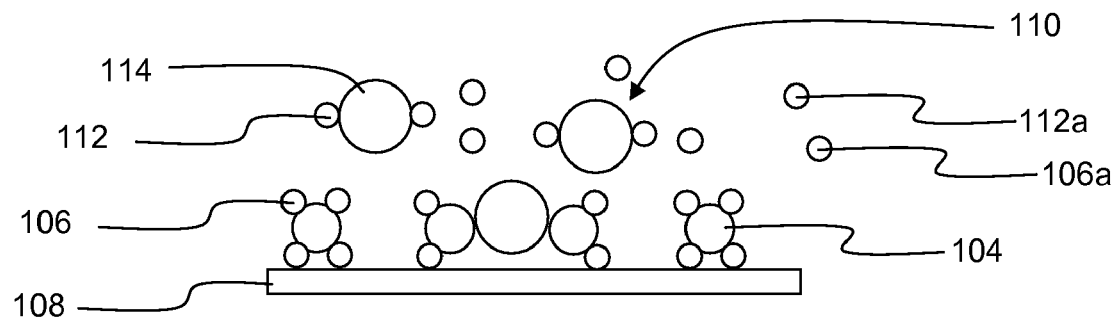
Figure 1C:
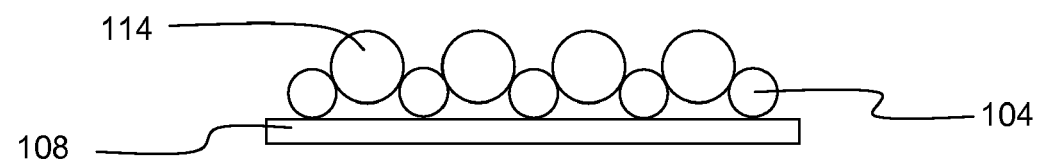

FIGS. 1A, 1B, and 1C illustrate a cycle of an exemplary atomic layer deposition method in a series of operations in accordance with an embodiment of the present invention. FIG. 1A shows the introduction of precursor 102 such as $SiCl_4$ made up of silicon 104 and chlorine 106. A monolayer of $SiCl_4$ forms on substrate 108. FIG. 1B shows the introduction of a second precursor 110 such as $H_2O$ made up of hydrogen 112 and oxygen 114. When precursors 102 and 110 react, free hydrogen 112a and free chlorine 106a may be released. As shown in FIG. 1C, when the reactions are complete, a monolayer such as of $SiO_2$ made up of oxygen 114 and silicon 104 may remain. As indicated above, a cycle is defined as one pulse of the first precursor, purge, one pulse of the second precursor, purge, and so on. In an embodiment, the sequence may then be repeated until the final desired thickness is reached.

In embodiments of the present invention, suitable coating materials that may be deposited using ALD include oxides and nitrides, such as silicon dioxide ($SiO_2$), aluminum oxide ($Al_2O_3$), titanium dioxide ($TiO_2$), zirconium dioxide ($ZrO_2$), tantalum oxide ($Ta_2O_5$), titanium nitride (TiN), aluminum nitride (AlN), etc. The exemplary coating materials identified above are the materials which are desired in the final coating layer(s), although it should be understood that various precursor materials may be used to provide such suitable resultant coating materials. For example, a coating material of aluminum oxide may be achieved by reacting $Al(CH)_3$ and $H_2O$ or $O_3$ precursors, a coating material of silicon dioxide may be achieved by reacting $SiCl_4$ and $H_2O$ precursors, and a coating material of titanium nitride may be achieved by reacting $TiCl_4$ or $TiI_4$ and $NH_3$ precursors.

In embodiments of the present invention, ALD may be used to deposit coating materials on a variety of dental devices and fixtures, including crowns, wires (such as orthodontic wires), plates, bridges, orthodontic brackets, braces, denture clasps, denture frameworks, implants, inlays, onlays, etc.

In embodiments, such dental devices and fixtures may be constructed from or coated with various materials, such as metals and/or alloys, such as titanium, titanium-aluminum-vanadium, stainless steel, cobalt-chromium, nickel-chromium, nickel-titanium, etc. for example as used for stainless steel crowns or nickel-titanium (NiTi) orthodontic wires. In embodiments, the device or fixture may be constructed from a biocompatible material or, in embodiments, a material that is not biocompatible, as the coating(s) applied thereto may render the device/fixture biocompatible.

In a further embodiment, ALD may be used to deposit suitable coating materials on a variety of orthopedic implants or related devices, such as wires, pins, screws, disks, plates, brackets, splints, etc.

In an embodiment, an ALD coating may be applied to reduce or eliminate ion leakage from an underlying substrate or surface material such as nickel leakage from a stainless steel disk or wire. The extent of the reduction in the rate of ion release is dependent on the thickness of the deposited layers and the completeness of coverage. In an embodiment, the use of an ALD coating may reduce ion leakage from a substrate by 60%-90% to as much as 100%, for example at least 60%, at least 80%, or at least 90%.

In an exemplary embodiment of the present invention, circular samples (15.3 mm diameter) of type 305 stainless steel were punched from a foil 0.3 mm thick. The stainless steel samples were cleaned and coated with an approximately 60 nm thick titanium dioxide coating using an ALD process. The samples were immersed in a corrosion solution in accordance with methods following the ISO 10271:2001 and ANSI/ADA Specification No. 97. Corrosion tests were performed for 1 hour, 10 hours and 100 hours of immersion. The resulting test solutions were analyzed by inductively coupled plasma mass spectroscopy (ICP-MS) to determine the ion concentration of iron (Fe), nickel (Ni), and chromium (Cr) released from the samples into the test solutions.

Figure 2A:
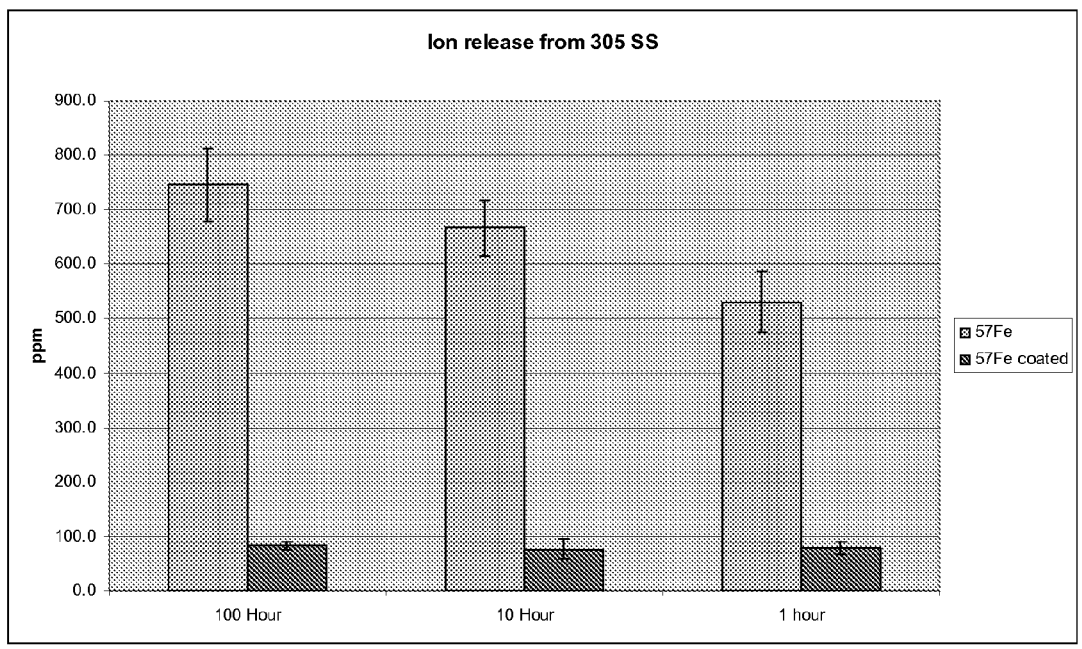
FIGS. 2A, 2B, and 2C are graphs of the results of the testing of ion leakage from samples with and without a coating in accordance with an embodiment of the present invention.
Figure 2B:
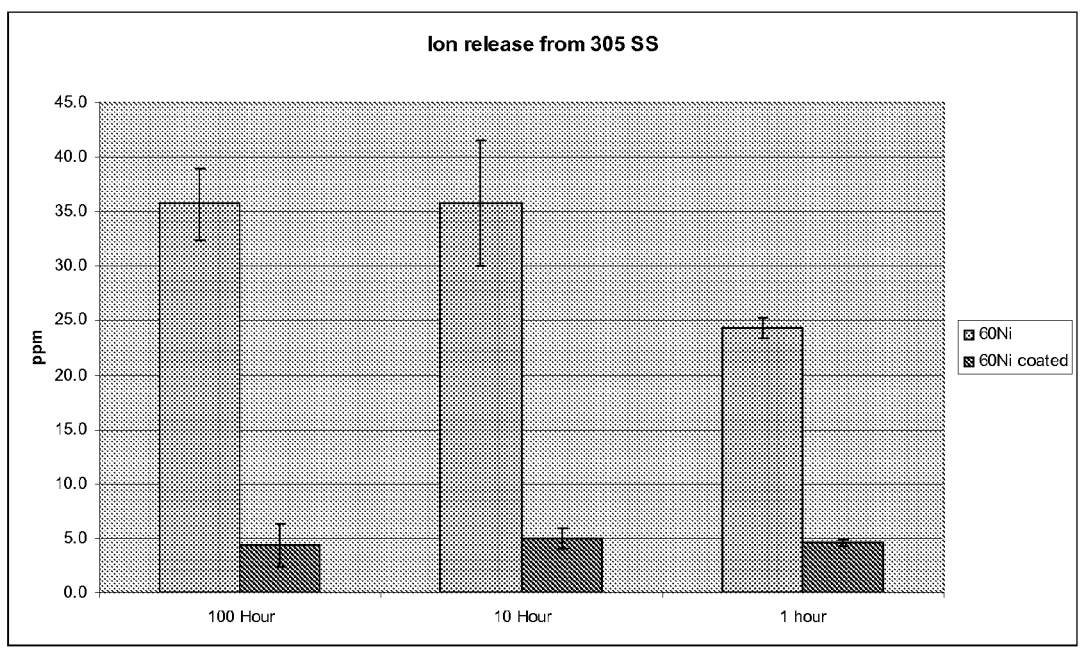
Figure 2C:
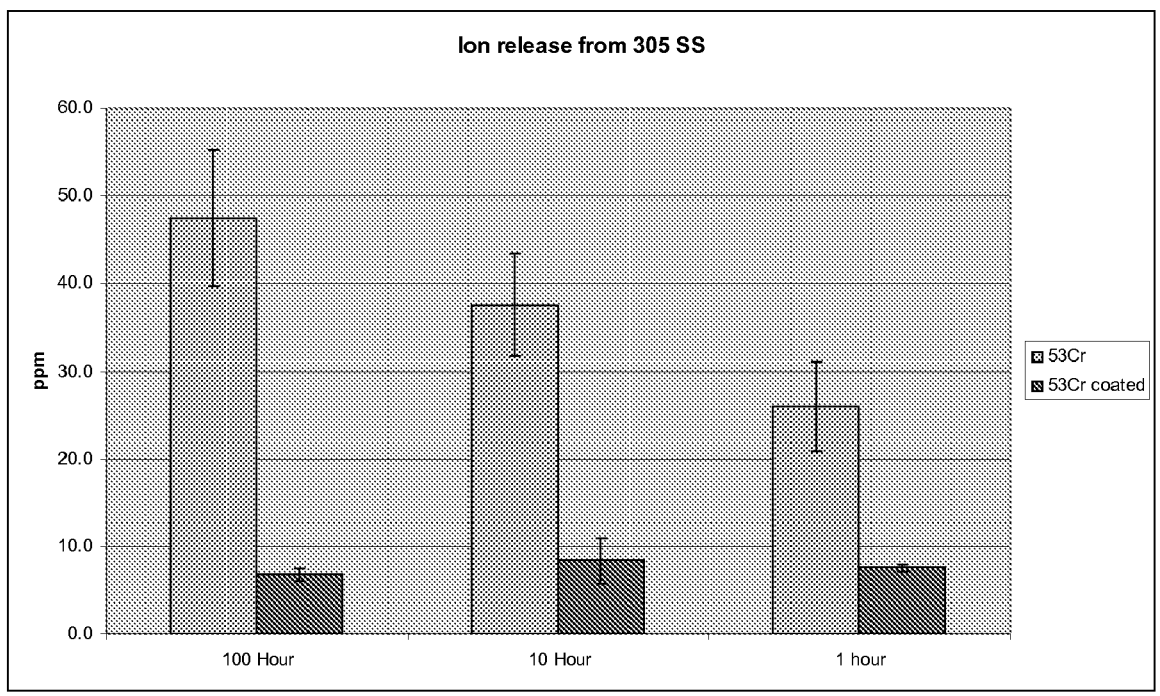

FIGS. 2A, 2B, and 2C are graphs of the results of the testing of ion leakage from the samples with and without a coating in accordance with an embodiment of the present invention. The graphs indicate ion release from samples of coated and uncoated alloys. As seen, the concentration of ions released from the samples was extremely low, and was essentially below the minimum detectable limits of each ion in the coated samples. Clearly, the coating provides substantial protection from ion leakage as compared to the uncoated samples. In addition, in the coated samples, there is little or no change in the leakage characteristic of the samples over time. In contrast, in the uncoated samples, there is a time-dependent linear leakage shown.

In an embodiment, a suitable coating material may be deposited in a multilayered film or coating of 15-250 nm, such as less than about 200 nm, for example less than 100 nm thick, such as approximately 40-90 nm thick.

While ALD is primarily referred to throughout the description, it should be appreciated that in certain embodiments other deposition methods may be utilized in accordance with the teachings herein. For example, a chemical vapor deposition method may be used to apply coatings on dental and/or orthopedic devices, although such coatings tend to be thicker than the coatings generated using ALD.

In an embodiment, a pigmented coating may be applied to a surface to mask or cover the underlying material. An ALD thin film coating may be characterized as producing an interference color for which the color variance is dependent on the angle at which the observer views the coating. However, pigmentation typically achieves color characteristics from light scattering rather than interference. Thus, in an embodiment, a plurality of pigment particles may be coated on or dispersed on such a surface prior to, during, and/or after ALD coating.

In an embodiment, a pigment may be provided in conjunction with a thin film to form a colored or pigmented thin film. Pigmented thin films may be used to increase the aesthetics of the surface to which the film is applied, and may also impart additional beneficial functional and/or structural properties. Such a pigmented thin film may be used, for example, to coat or cover a dental alloy. In an embodiment, a pigmented thin film may be provided that is white, or off-white to simulate the color of a tooth. In other embodiments, colors other than white or off-white may be produced, as desired.

A variety of colors may utilized on devices as discussed above, and, in an embodiment, such colors may be used to match devices to their intended use, or to match devices to each other in a system, for example an orthodontic bracket system, an orthopedic construct, etc. where like devices have like colors, and so on.

In an embodiment, a surface to be coated may be painted, or alumina or zirconia powders (which are readily available as polishing powders) or rare earth pigments may be mixed into thin slurries and applied to a desired surface to pigment the surface. In an embodiment, pigment may be applied with a binder (such as polyvinyl alcohol (PVA)), which may be burned-off, for example at a temperature of approximately 200° C. leaving behind the pigment particles.

In embodiments, the thickness of the coatings may be utilized to control the color characteristics of the coatings. For example, with very thin coatings, such as approximately 15 nm, the coating may be imperceptible, while with thicker coatings, such as 40-45 nm, interference colors may be visible. In an embodiment, with even thicker coatings, such as approximately 80 nm, pigment may be incorporated into the coatings.

Figure 3:
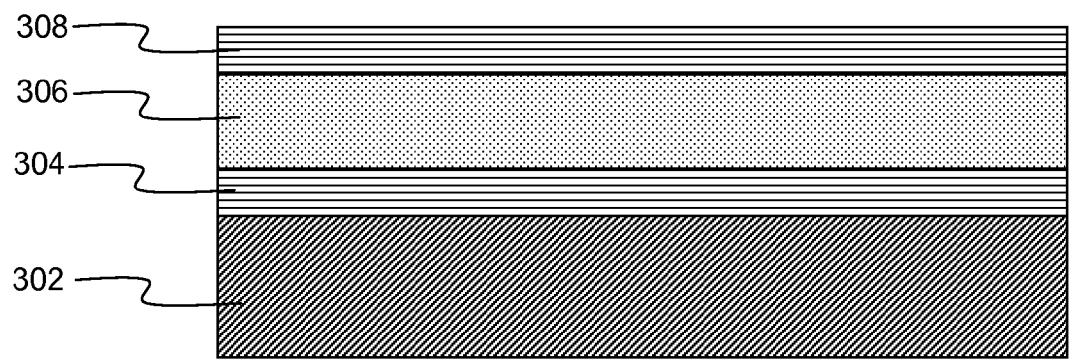
FIG. 3 illustrates an exemplary coated and pigmented substrate in accordance with various embodiments of the present invention.

An exemplary coated and pigmented substrate may be seen in FIG. 3. FIG. 3 shows substrate 302 coated by one or more coating layers 304. Pigment 306 may be applied to coating layers 304 in a variety of thicknesses. In an embodiment, coating layer 304 may be absent and pigment 306 may be applied directly to substrate 302. In an embodiment, one or more coating layers 308 may be applied to pigment 306 to complete the coating. In an embodiment, because a thin film of coating layer(s) 308 may be optically transparent, the color of underlying pigment 306 may be seen.

In an embodiment, coating layers 304 and 308 may be applied/deposited using ALD. In an embodiment, coating layers 304 and 308 may be the same material, and in another embodiment coating layers 304 and 308 may be different materials.

In an embodiment, a plurality of pigment layers may be applied alternating with one or more layers of coating material.

In an embodiment, a coating layer may be applied directly to a substrate, or a coating layer (or layers) may be deposited on a substrate prior to, with, or after application of pigment. In an embodiment, pigment may be applied with a binder, which may be burned-off after application.

Thus, in an embodiment, a coating composition may be provided comprising a layer of pigmented material, and one or more layers of an oxide or nitride disposed on, in, and/or under the layer of pigmented material.

In an embodiment, a method of coating a substrate is provided. Such a method may entail cleaning the surface of the substrate to be coated. In an embodiment, the surface may then be coated with one or more coating layers. Next, a quantity of pigment may be applied to the coating layer(s) and then the binder, if any, may be heated/burned off. When the binder is removed, a porous matrix of pigment may remain. Next, one or more applications/depositions of coating material may be provided to fill-in the various pores in the pigment matrix to form a dispersion matrix. In an embodiment, coating layers may be formed by an ALD process as discussed herein.

Figure 4:
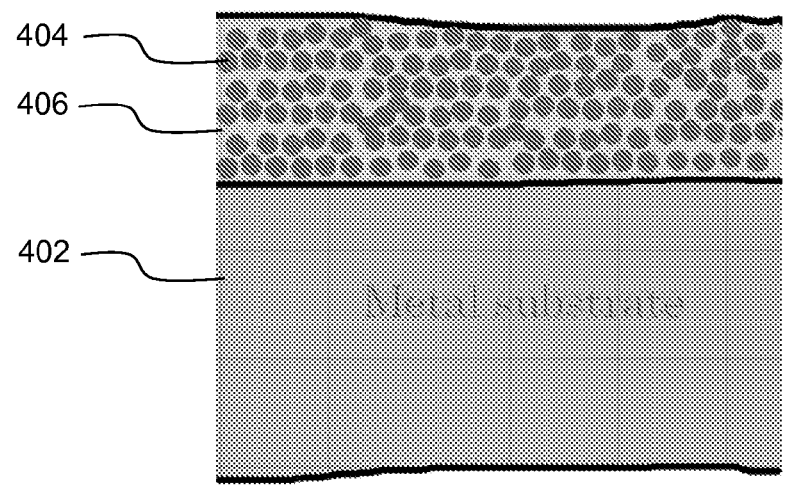
FIG. 4 illustrates a pigment matrix coating on a substrate in accordance with various embodiments of the present invention.

In an embodiment as shown in FIG. 4, a pigment matrix coating on a substrate is provided. On substrate 402 may be found pigment 404 in a matrix surrounded by and integral with coating material 406. Coating material 406 may be a coating material as described herein and may be applied, for example, using ALD.

In an embodiment of the present invention, the coatings described herein may provide strong mechanical strength adherence to various substrates. In another embodiment, coatings as described herein may provide increased lubricity of the surface as compared to the uncoated surface, thus reducing discomfort, for example experienced sometimes with dental devices.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method of coating a substrate, comprising:
    applying a plurality of pigment particles to a surface of the substrate; and
    after applying the pigment particles, forming at least one thin film layer on the substrate by atomic layer deposition to form a coating layer including the pigment particles dispersed therein to coat at least a portion of the surface of the substrate.

2. The method of claim 1, wherein said substrate comprises at least one of titanium, titanium-aluminum-vanadium, stainless steel, cobalt-chromium, nickel-chromium, and nickel-titanium.

3. The method of claim 1, wherein said at least one thin film layer comprises an oxide or a nitride.

4. The method of claim 1, wherein said at least one thin film layer comprises silicon dioxide, aluminum oxide, titanium dioxide, zirconium dioxide, tantalum oxide, titanium nitride, or aluminum nitride.

5. The method of claim 1, wherein said substrate is at least a portion of a dental device.

6. The method of claim 5, wherein said dental device comprises a crown, wire, plate, bridge, orthodontic bracket, brace, denture clasp, denture framework, implant, inlay, or onlay.

7. The method of claim 1, wherein said substrate is at least a portion of an orthopedic device.

8. The method of claim 7, wherein said orthopedic device comprises a wire, pin, screw, disk, plate, bracket, or splint.

9. The method of claim 1, wherein said substrate comprises an alloy and wherein said coating provides a reduction of ion leakage from said alloy in an amount of at least 60% in comparison to said alloy without said coating.

10. The method of claim 1, wherein said substrate comprises an alloy and wherein said coating provides a reduction of ion leakage from said alloy in an amount of at least 80% in comparison to said alloy without said coating.

11. The method of claim 1, wherein providing a substrate comprises providing a biocompatible substrate.

12. The method of claim 1, wherein said at least one thin film layer forms a coating having a thickness of approximately 15-250 nm.

13. The method of claim 1, wherein said at least one thin film layer forms a coating having a thickness of approximately 40-90 nm.

14. The method of claim 1, wherein dispersing pigment particles within the at least one thin film layer comprises dispersing an alumina or zirconia powder within the at least one thin film layer.

15. The method of claim 1, wherein dispersing pigment particles within the at least one thin film layer comprises dispersing rare earth pigment particles within the at least one thin film layer.

16. The method of claim 1, wherein dispersing pigment particles within the at least one thin film layer comprises dispersing pigment particles in combination with a binder within the at least one thin film layer.

17. The method of claim 16, further comprising burning off the binder.

18. The method of claim 17, wherein burning off the binder forms a porous matrix of pigment particles, the method further comprising applying at least one additional thin film layer to at least partially fill pores of the porous matrix.

19. The method of claim 17, wherein burning off the binder comprises burning off the binder at a temperature of approximately 200° C.

20. A method of coating a substrate, comprising:
    applying a plurality of pigment particles in combination with a binder to a surface of a substrate;
    burning off the binder to form a porous matrix of pigment particles; and
    depositing at least one thin film layer to further coat the substrate and at least partially fill pores of the porous matrix and form a dispersion matrix of pigment particles,
    wherein depositing at least one thin film layer comprises depositing at least one thin film layer by atomic layer deposition.

21. The method of claim 20, wherein depositing at least one thin film layer comprises depositing at least one thin film layer of an oxide or nitride.

* * * * *